United States Patent [19]

Hagen

[11] Patent Number: 4,745,808
[45] Date of Patent: May 24, 1988

[54] MEASUREMENT APPARATUS UTILIZING SONAR WAVES

[76] Inventor: John H. Hagen, 15415 N. 30th Ave., Phoenix, Ariz. 85023

[21] Appl. No.: 941,682

[22] Filed: Dec. 15, 1986

[51] Int. Cl.⁴ .............................................. G01B 17/02
[52] U.S. Cl. ....................................... 73/597; 367/902
[58] Field of Search ...................... 73/597, 290 V, 1 J; 386/381; 318/603; 367/104, 902

[56] References Cited

U.S. PATENT DOCUMENTS

| | | | |
|---|---|---|---|
| 2,661,714 | 10/1951 | Greenwood et al. | 73/290 V |
| 3,108,469 | 10/1963 | Dyer et al. | 73/597 |
| 4,356,439 | 10/1982 | Mott et al. | 318/685 |
| 4,528,491 | 7/1985 | Takeuchi et al. | 318/603 |

Primary Examiner—Stewart J. Levy
Assistant Examiner—Robert P. Bell
Attorney, Agent, or Firm—H. Gordon Shields

[57] ABSTRACT

Measurement apparatus utilizes a sonar head for sending and receiving sonar signals and the apparatus is calibrated before each measurement by locating the sonar head a fixed, predetermined distance from a stationary target. Movement of the sonar head is accomplished by a stepper motor and lead screw arrangement to position the sonar head the same, predetermined distance from the element to be measured as it was originally placed for calibration, and the difference between the calibration distance and the second distance is from a target motor and lead screw arrangement to position the sonar head the same, predetermined distance from the element to be measured as it was originally placed for calibration, and the difference between the calibration distance and the second distance is translated into a distance representing the desired measurement.

15 Claims, 1 Drawing Sheet

U.S. Patent
May 24, 1988
4,745,808
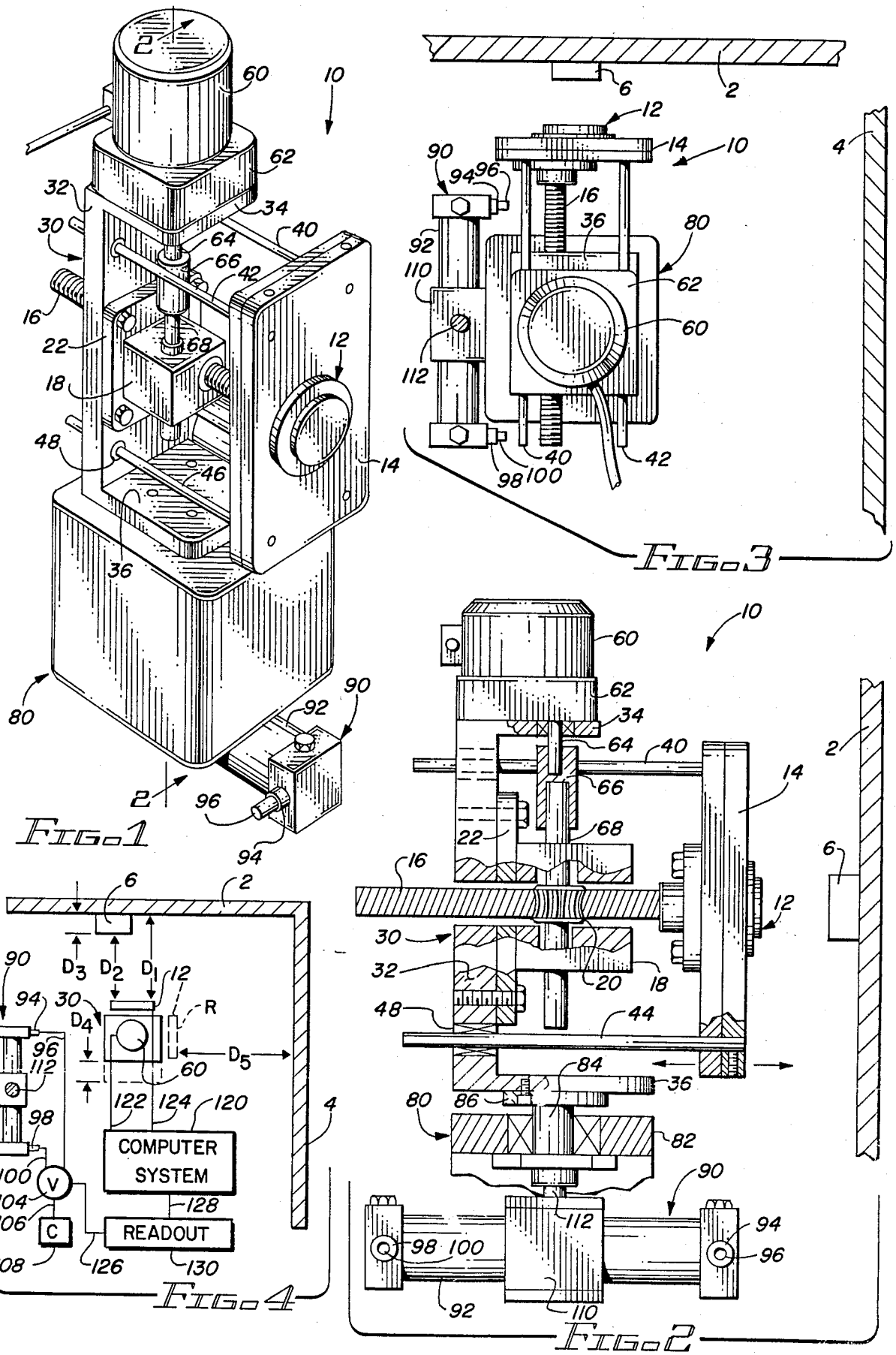

MEASUREMENT APPARATUS UTILIZING SONAR WAVES

BACKGROUND OF THE INVENTION

1. Field of the Invention:

This invention relates to measurement apparatus and, more particularly, to measurement apparatus utilizing a sonar head for sending and receiving sonar signals and for using the sonar signals for measuring relatively small distances very accurately.

2. Description of the Prior Art:

Obviously, there are various ways of measuring work in terms of relatively small distances. To begin with, measurement of small distances is typically made from a relatively flat surface. Mechanical elements may be used to measure upwardly from the flat surface to the top of the work to be measured. Such measurements are typically made by mechanical elements, such as measuring and the like.

For measuring horizontal distances, laser beams may be used for measuring both small and large distances. A laser beam, typically a pulse laser beam, is reflected from a target, and the length of time between the sending and the receiving of the laser pulses is measured to determine the distance.

For measuring the thickness of a work, such as the thickness of a film, relatively sophisticated equipment is generally required. Obviously, the utilization of mechanical elements for measuring relatively thin film, in terms of four or five or six decimal places for centimeters, millimeters, or inches, or the like, mechanical measuring apparatus is obviously incapable of providing accurate results. Hence, it is typically necessary to use some type of electronic measuring apparatus or measuring apparatus that utilizes some type of energy beam, in which the energy is reflected from the target work and is compared with a reference figure. Such apparatus is generally relatively expensive and is relatively complicated in terms of usage and is relatively time consuming in terms of the time required to make a measurement.

The apparatus of the present invention utilizes sonar energy, and is relatively inexpensive to use, relatively fast in providing the desired information, and is relatively easy to use. A microcomputer is utilized with the apparatus of the present invention to keep track of the distance a stepper motor moves in moving the sonar head to provide a predetermined distance from a target which is equal to the predetermined reference or calibration distance originally established by the apparatus.

SUMMARY OF THE INVENTION

The invention described and claimed herein comprises a sonar head spaced apart from a reference location and a stepper motor coupled to the sonar head for moving the sonar head relative to the fixed location and relative to work to be measured which is disposed against a reference location. A microcomputer is utilized to measure the distance the stepper motor moves the sonar head in providing the same distance from the work to be measured as the sonar head was located from the reference location. For measuring continuously moving elements, such as a moving film disposed against the fixed location, a second fixed reference location is used and the stepper motor and sonar head assembly is rotated ninety degrees for continuous calibration of the sonar head.

Among the objects of the present invention are the following:

To provide new and useful measurement apparatus;

To provide new and useful apparatus for measuring relatively small distances;

To provide new and useful measurement apparatus utilizing a sonar head;

To provide new and useful measuring apparatus including a sonar head moved by a stepper motor;

To provide new and useful measurement apparatus utilizing a fixed base element and a sonar head movable relative to the fixed base element for measuring the thickness of work disposed against the fixed base element;

To provide new and useful measurement apparatus utilizing a sonar head movable by a stepper motor which continually is calibrated from a fixed reference location and which includes a stepper motor for moving the sonar head and a microcomputer for measuring the distance the stepper motor uses the sonar head from the fixed reference; and To provide new and useful measurement apparatus including a first fixed reference and a second fixed reference disposed substantially ninety degrees from the first fixed reference, and the sonar head is rotated to the second fixed reference for calibration purposes when a continuous element to be measured is disposed adjacent to the first fixed reference.

BRIEF DESCRIPTION OF THE DRAWING

FIG. 1 is a perspective view of a portion of the apparatus of the present invention.

FIG. 2 is a view in partial section taken generally along line 2—2 of FIG. 1, illustrating the apparatus of the present invention in its use environment.

FIG. 3 is a top plan view illustrating the operation of the apparatus of the present invention.

FIG. 4 is a schematic representation illustrating the operation of the apparatus of the present invention.

DESCRIPTION OF THE PREFERRED EMBODIMENT

FIG. 1 is a perspective view of apparatus 10 of the present invention. FIG. 2 is a view of the apparatus of FIG. 1, taken generally along line 2—2 of FIG. 1. FIG. 3 is a top view of the apparatus 10 of FIGS. 1 and 2. For the following discussion, reference will primarily be made to FIGS. 1, 2 and 3.

Apparatus 10 includes a sonar head 12 secured to a support plate 14. The support plate 14 is in turn secured to one end of a threaded shaft or lead screw 16. The lead screw 16 extends through a gear box 18. As shown in FIG. 2, within the gear box 18 is a gear 20 which meshes with the lead screw 16.

The gear box 18 is secured to a support plate 22, and the support plate 22 is in turn secured to a bracket 30. The bracket 30 includes a back plate 32, which is directly secured to the support plate 22. The bracket 30 also includes a top plate 34 and a bottom plate 36. The top and bottom plates 34 and 36 are appropriately secured, as by welding, to the back plate 32. The top and bottom plates are substantially parallel to each other and are substantially perpendicular to the back plate 32.

The sonar head 12, secured to the support plate 14, moves in response to the rotation of the lead screw 16. The support plate 14 is guided with respect to the bracket 30 by four guide rods, including a top guide rod 40, a top guide 42, a bottom guide 44, and a bottom guide rod 46. The guide rods 40 ... 46 extend through linear bearings, such as linear bearing 48 (See FIGS. 1 and 2), which extend through the back plate 32 of the bracket 30. The guide rods are appropriately secured to the support plate 14.

The bracket 30, through its bottom plate 36, is appropriately secured for rotation on a base 80.

Rotation of the lead screw 16 to move the sonar head 12 linearly relative to the bracket 30 is accomplished by means of a reversible stepper or stepping motor 60. The stepper motor 60 is secured to a gear box 62. The gear box 62 is in turn secured to the top plate 34 of the bracket 30. An output shaft 64 extends downwardly from the gear box 62. The output shaft 64 is coupled to a shaft 68 through a coupling element 66. The gear 20 is secured to the shaft 68, and rotates therewith. Rotation of the shafts 64 and 68 causes rotation of the gear 20, and rotation of the gear 20 causes linear movement of the lead screw 16. The linear movement of the lead screw 16 in turn results in linear movement of the support plate 14 and the sonar head 12 secured thereto. The stepper motor 60 is thus coupled to the lead screw 16, which does not rotate through the shafts 64 and 68 and the gear 18. It will be noted that the meshing of the threads of the lead screw 16 and the gear 20 provides generally a more precise control of the movement of the sonar head 12 than may be accomplished with a standard or typical rack and pinion arrangement.

As may best be understood with reference to FIG. 2, the fixed base 80 includes a top plate 82. A shaft 84 extends through, and is appropriately journaled for rotation in, the top plate 82. The shaft 84 is appropriately secured to a plate 86, and the plate 86 is appropriately secured to the bottom plate 36 of the bracket 30. Rotation of the shaft 84 results in rotation of the plate 86 and of the plate 36 and the bracket 30, and accordingly of the sonar head 12 and the motor 60, and their various elements, all secured to the bracket 30.

Rotation of the shaft 84, and of the bracket 30, and the associated elements, is accomplished by means of an air motor 90. The air motor 90 includes a cylinder 92 in which is disposed a piston, as is well known and understood in the art. At opposite ends of the cylinder 92 are appropriate input/exhaust ports, including an input/exhaust port 94 and an input/exhaust port 98. The ports 94 and 98 are best shown in FIGS. 2 and 3. In FIG. 3, a conduit 96 is shown secured to the port 94, and a conduit 100 is shown secured to the port 98. The conduit 96, and its port 94, are also shown in FIG. 1.

The air motor 90 is coupled to the shaft 84 through a gear box 110. An actuator shaft 112 extends upwardly from the gear box 110 and is appropriately secured to the shaft 84. Movement of the piston within the cylinder 92 of the air motor 90 results in a ninety degree rotation of the shaft 84 through the gear box 110 and the shaft 112. The bracket 30 and the sonar head 12 accordingly rotate ninety degrees when the air motor 90 is actuated.

The air motor 90 rotates the bracket 30 back and forth, through the ninety degrees. For rotation in one direction, one of the ports 94 and 96 is the input port and the other port is the exhaust port. For rotating the bracket ninety degrees in the opposite direction, the input and exhaust ports are reversed: the exhaust port becomes the intake port and the intake port becomes the exhaust port.

In FIG. 2, the sonar head 12 is shown disposed adjacent to, but spaced apart from, a fixed reference base or wall 2 with work 6 disposed against the wall or fixed reference base. With the work 6 removed from in front of the sonar head 12, the distance from the sonar head 12 to the wall 2 may be accurately measured. In practice, the sonar head 12 is moved by movement of the stepper motor 60 until it is at a predetermined distance from the wall 2. The work 6 is then placed against the wall 2. The thickness of the work 6 is to be measured. The measurement is accomplished by moving the sonar head 12 rearwardly, as viewed in FIG. 2, or to the left, until the distance between the sonar head 12 and the front face of the work 6 is the same as the predetermined distance between the sonar head 12 and the wall 2. The distance which the sonar head 12 moves rearwardly until the two distances are equal is the thickness of the work 6, or the distance to be measured. This is illustrated in detail in FIG. 4.

FIG. 4 is a schematic representation of the operation of the apparatus 10 of the present invention. The sonar head 12 is schematically illustrated spaced apart a distance D1 from the wall 2. The work 6 is shown disposed against the wall 2, and its thickness is represented by D3. The distance between the sonar head 12 and the work 6 is schematically illustrated as D2. Prior to the work 6 being placed against the wall 2, the sonar head 12 is moved until it is at the fixed, predetermined distance D1 from the wall 2. Then, the work 6 is placed against the wall 2. Its thickness, D3, is the finite distance to be measured.

With the work 6 against the wall 2, the sonar head measures the distance D2 from the front face of the work 6. The stepper motor 60 is then actuated, under control of a computer system or microprocessor 120. The computer system 120 is coupled to the stepper motor 160 by an appropriate cable 122. The computer system 120 causes the stepper motor 60 to be actuated until the distance between the sonar head 12 and the work 6 is again at the distance D1. This movement of the stepper motor 12 is illustrated in dotted line in FIG. 4. The rearward distance moved by the sonar head 12 until the distance D1 was again determined is illustrated as D4. Since the computer 120 keeps track of the number of steps moved by the stepper motor 60, and each step is allocated a specific, finite distance, adding up the total number of steps moved by the stepper motor 60, and each step is allocated a specific, finite distance, adding up the total number of steps moved in the D4 movement determines the thickness of the work 6. Algebraically, since D4 equals D3, the rearward movement of the sonar head 12, or D4, is equal to the D3 thickness of the work 6.

It will be noted that the original measurement, the D1 distance between the sonar head 12 and the wall 2, before the work 6 is placed against the wall 2, is the primary measurement. That primary measurement, then, is used to measure the thickness of the work 6. If the work 6 were a continuous element, such as a continuous film, then there could not be a base or primary measurement for calibration purposes between the sonar head 12 and the wall 2. The purpose, then of the wall 4 and of the air motor 90, and its associated elements, including the shafts 112 and 84 and the bracket 30, is to rotate the sonar head 12 so that it may obtain a base or primary, calibration distance measurement from the wall 4.

As best illustrated in FIG. 4, but as also may be understood from FIG. 3, the center or axis of rotation of the bracket 30 is the centerline or axis of the shafts 112 and 84. This axis of rotation or centerline intersects the centerline of the lead screw 16. The centerline of the sonar head 12 is aligned with the centerline or axis of the lead screw 16. Thus, the sonar head 12 will be the same distance from the wall 2 that it is from the wall 4 when the sonar head 12 is rotated by the air motor 90 from the position shown in FIGS. 2, 3, and 4, facing the wall 2, until it is directed toward the wall 4. Thus, the distance D5, shown in FIG. 4, equals the distance D1, with D5 being the distance from the sonar head 12 to the wall 4. Obviously, the walls 2 and 4 are substantially perpendicular to each other, and the centerline or axis of rotation of the shaft 112 is equidistance from the walls 2 and 4.

From the preceding paragraphs, it will be understood that, if the work 6 is a continuous film passing in front of the wall 2, the sonar head 12 will be rotated ninety degrees by the air motor 90 so that a base or primary measurement, for calibration purposes, may be obtained from the wall 4. Then, when the air motor 90 is again actuated to rotate the sonar head 12 back towards the wall 2, the sonar head has, in effect, obtained a calibration measurement from the wall 2, since the distance D1 from the sonar head 12 to the wall 2 is the same as the distance D5 from the sonar head 12, as rotated ninety degrees, to the wall 4. Thus, the thickness of the work 60, a continuous film, may still be measured by the procedure discussed above.

Actuation of the sonar head 12 is accomplished, for measurement purposes, by signals from the computer system 120 through a cable 124. The computer system 120 includes a microcomputer or microprocessor, as discussed above, and other appropriate elements for controlling the movement of the stepper motor 60 and of the air motor 90, as required, and for controlling the sonar head 12, including causing the sonar head 12 to transmit the required pulses or sonar waves for making the calibration measurements D1 and D5, and also the measurement D2 and D4 to measure the thickness of the work 6. The sonar head 12 includes both transmitting and receiving elements for transmitting sonar waves and for receiving the reflected sonar waves.

As has been discussed above, the air motor 90 requires a source of compressed air and appropriate valving for directing the compressed air to either the ports 94 or 98, as required, by means of the conduits 96 or 100, respectively. Such elements, with the appropriate valves, etc., are schematically shown in FIG. 4. It will be understood that the actuation of the valving required for operating the air motor 90 will be under the control of the computer system 120, or, if desired, it may be manually actuated by an operator.

In FIG. 4, the air motor 90 is schematically shown connected to a source of compressed air 108 through a two-way or reversible valve 104 by a conduit 106. The valve 104 is in turn connected to the air motor 90 through the conduits 96 and 100.

Actuation of the valve 104 to actuate the air motor 90, and thus to rotate the bracket 30 and the sonar head 12, is controlled by the computer system 120 through a control cable 126.

A readout of the thickness of the work 6 is provided through a readout apparatus 130. The readout apparatus is connected to the computer system 120 through an appropriate cable 128.

If a continuous film or other continuous element is not to be measured by the apparatus 10, then the air motor 90, and its associated elements, need not be provided as part of the apparatus of the present invention.

It is only when a continuous element, such as a continuous film, is to be measured that the rotation of the sonar head 12 must be accomplished. If the work 6 to be measured is not continuous, then the apparatus 10 may obtain a calibration reading, or a base reading, directly from the wall 2 before the work to be measured is placed against the wall 2.

It is obvious that the sonar head 12 is both a transmitter and receiver, as is common and well known in the art. Thus, the sonar head 12 includes a transmitter for transmitting sound waves and a transmitter for receiving the reflected sound waves.

It will be understood that the apparatus of the present invention is able to measure relatively small distances. It will also be understood that, since the sonar head 12 is calibrated in terms of the speed of sound, only the temperature and humidity are variables. The system must be recalibrated only after changes in either temperature or humidity. In practice, it may be desirable to insure consistent, continuous accuracy, to recalibrate the sonar head 12 by making the base measurement from the sonar head 12 to the wall 2 or to the wall 4 on a regular basis, or throughout the various measurements made during the course of a day. This will eliminate any possible errors that may occur as the temperature changes during the day and/or as the humidity changes during the day.

Also, as has been stated above, an important ingredient in the accuracy of the measurements of the present invention is the gradation in the steps included in the stepper motor 60. Providing the individual steps are small enough, the apparatus of the present invention is capable of making measurements in terms of millionths of a second.

For some circumstances, in which extreme or ultimate accuracy in measurements is desired, the coupling element 66, and the shaft 68, may be omitted. The shaft 64 accordingly may be extended to the gear box 18 and may have the drive gear 20 secured directly to it.

While the principles of the invention have been made clear in illustrative embodiments, there will be immediately obvious to those skilled in the art many modifications of structure, arrangements, proportions, the elements, materials, and components used in the practice of the invention, and otherwise, which are particularly adapted for specific environments and operative requirements without departing from those principles. The appended claims are intended to cover and embrace any and all such modifications, within the limits only of the true spirit and scope of the invention. This specification and the appended claims have been prepared in accordance with the applicable patent laws and the rules promulgated under the authority thereof.

What I claim is:

1. Sonar measurement apparatus for measuring the thickness of a work, comprising, in combination:
   sonar transmitting and receiving means;
   reference base means, including a first reference base and a second reference base;
   means for moving the sonar transmitting and receiving means linearly with respect to the reference base means to obtain a first predetermined distance measurement before the work to be measured is placed against the reference base means, and then for moving the sonar transmitting means linearly with respect to the work to be measured to obtain a second predetermined measurement distance which is equal to the first predetermined distance measurement, and including means for rotating the sonar means relative to the first reference base and the second reference base to obtain the first predetermined distance from the first reference base and the second predetermined distance from the work disposed against the second reference base; and means for measuring the distance the sonar transmitting and receiving means moves between the first and second predetermined measurements, which distance represents the thickness of the work.

2. The apparatus of claim 1 in which the means for moving the sonar transmitting and receiving means further includes a stepper motor coupled to the sonar transmitting and receiving means.

3. The apparatus of claim 2 in which the means for moving the sonar transmitting and receiving means further includes a lead screw coupled to the stepper motor, and the lead screw is secured to the sonar transmitting and receiving means.

4. The apparatus of claim 3 in which the means for measuring the distance includes computer means for controlling the stepper motor to obtain the first predetermined distance and the second predetermined distance and for determining the distance moved by the sonar transmitting and receiving means between the first and second predetermined distances to determine the thickness of the work.

5. The apparatus of claim 3 in which the means for measuring the distance further includes readout means for reading out the distance the sonar transmitting and receiving means moves between the first and second predetermined measurements.

6. The apparatus of claim 1 in which the sonar transmitting and receiving means includes
a sonar head, and
a plate secured to the sonar head and movable linearly towards and away from the reference base means.

7. The apparatus of claim 6 in which the sonar transmitting and receiving means further includes a base, and the plate and sonar head are secured to the base for linear movement.

8. The apparatus of claim 7 in which the means for moving the sonar transmitting means includes a reversible stepper motor coupled to the plate.

9. The apparatus of claim 8 in which the means for moving the sonar transmitting means further includes a lead screw secured to the plate and a rotating shaft coupled to the reversible stepper motor, and the lead screw is coupled to the rotating shaft to move the lead screw and the plate and sonar head.

10. Sonar measurement apparatus for measuring the thickness of a work, comprising, in combination:
sonar means for transmitting sonar pulses and for receiving reflected sonar pulses;
base reference means, including a first reference and a second reference base;
means for moving the sonar means relative to the base reference means to obtain a first predetermined distance measurement from the base reference means before the work is placed against the base reference means and for moving the sonar means linearly relative to the work after the work is placed against the base reference means to obtain a second predetermined distance measurement from the work which is equal to the first predetermined distance measurement, and including means for rotating the sonar means relative to the first reference base and the second reference base to obtain the first predetermined distance from the first reference base and the second predetermined distance from the work disposed against the second reference base; and
means for measuring the distance moved by the sonar means between the first and second predetermined distance measurements to determine the thickness of the work.

11. The apparatus of claim 10 in which the means for moving the sonar means includes a stepper motor having an output shaft rotatable in steps of a fixed, predetermined distance.

12. The apparatus of claim 11 in which the means for moving the sonar means further includes a threaded shaft secured to the sonar means and coupled to the output shaft of the stepper motor for moving the sonar means a fixed, predetermined distance in response to each step rotation of the stepper motor.

13. The apparatus of claim 12 in which the means for measuring the distance moved includes means for counting the steps moved by the stepper motor between the first and second predetermined distances.

14. The apparatus of claim 13 in which the means for moving the sonar means further includes a sonar head coupled to the threaded shaft.

15. The apparatus of claim 14 in which the means for moving the sonar means further includes a bracket coupled to the means for rotating the sonar means, and the sonar head and the threaded shaft and the stepper motor are secured to the bracket for joint movement.

* * * * *